United States Patent [19]
Komatsu et al.

[11] Patent Number: 4,766,258
[45] Date of Patent: Aug. 23, 1988

[54] PROCESS FOR PRODUCING HYDROCARBON FLUORIDE

[75] Inventors: Takahiro Komatsu; Tohru Ide; Hirohumi Akiyama; Takao Kitamura; Shinichi Yamamoto, all of Miyazaki, Japan

[73] Assignee: Asahi Kasei Kogyo Kabushiki Kaisha, Osaka, Japan

[21] Appl. No.: 817,379

[22] Filed: Jan. 9, 1986

[30] Foreign Application Priority Data

Jan. 9, 1985 [JP] Japan .................... 60-940

[51] Int. Cl.$^4$ ............................. C07C 17/10
[52] U.S. Cl. ................................ 570/168; 570/165
[58] Field of Search ................. 570/166, 168, 165

[56] References Cited

U.S. PATENT DOCUMENTS

| | | | |
|---|---|---|---|
| 2,005,708 | 6/1935 | Daudt et al. | |
| 2,452,975 | 11/1948 | Whalley | 570/168 |
| 2,495,407 | 1/1950 | Chapman et al. | 570/168 |
| 2,773,913 | 12/1956 | Goerrig et al. | 570/166 |
| 4,374,289 | 2/1983 | Van Der Puy et al. | 570/166 |

FOREIGN PATENT DOCUMENTS

| | | | |
|---|---|---|---|
| 2739478 | 3/1978 | Fed. Rep. of Germany | 570/166 |
| 39086 | 10/1972 | Japan | 570/166 |

*Primary Examiner*—J. E. Evans
*Attorney, Agent, or Firm*—Sughrue, Mion, Zinn, Macpeak & Seas

[57] ABSTRACT

A process for producing a hydrocarbon fluoride at a high selectivity with minimum formation of by-products is disclosed, which comprises reacting a hydrogen-containing hydrocarbon halide with anhydrous hydrogen fluoride in a liquid phase in the presence of a reaction product of (i) at least one of (a) an oxygen-containing compound selected from the group consisting of $H_2O$, $H_2O_2$ and an oxygen-containing organic compound, and (b) a nitrogen-containing compound selected from the group consisting of $NH_3$ and a nitrogen-containing organic compound, (ii) a tin compound selected from the group consisting of a stannic halide, a stannic oxyhalide and an organotin compound, and (iii) anhydrous hydrogen fluoride.

34 Claims, 3 Drawing Sheets

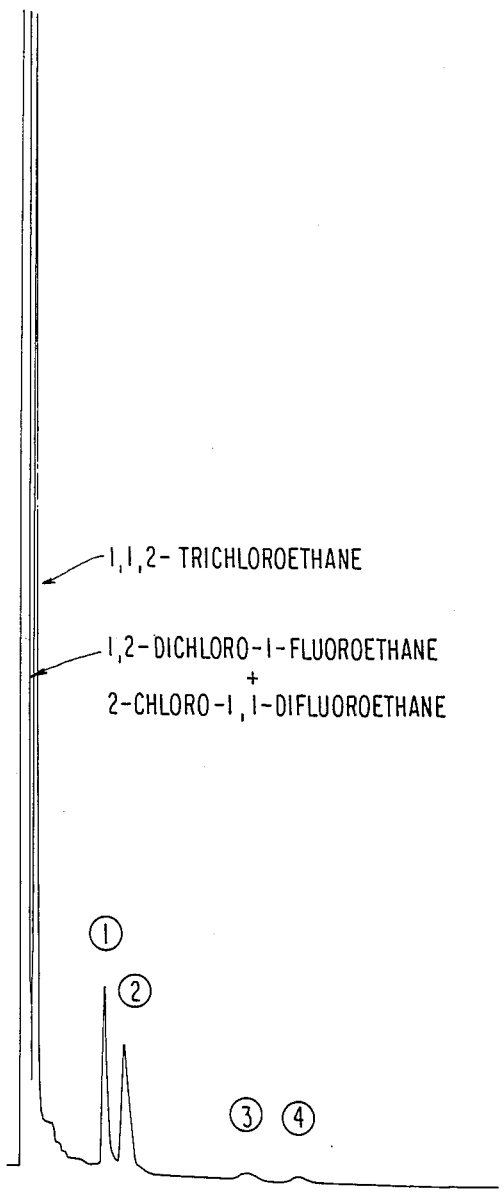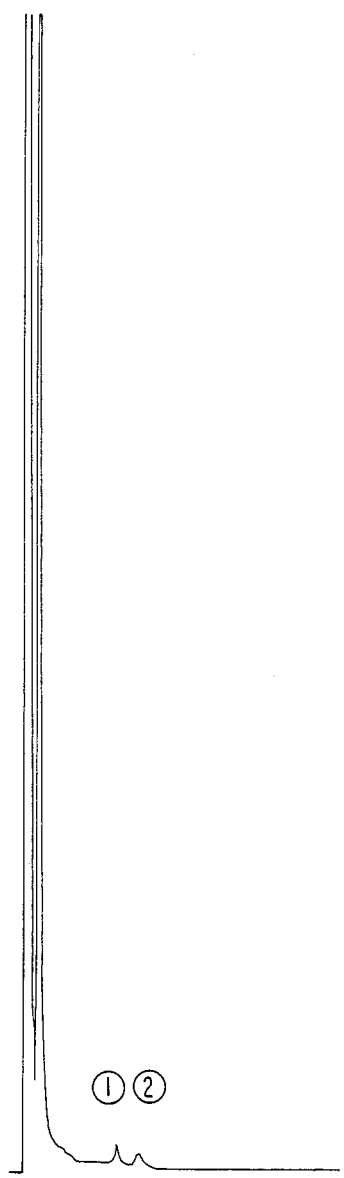
FIG. 3
FIG. 4

PROCESS FOR PRODUCING HYDROCARBON FLUORIDE

FIELD OF THE INVENTION

The present invention relates to a process for producing a hydrocarbon fluoride by reacting a hydrogen-containing hydrocarbon halide with anhydrous hydrogen fluoride in a liquid phase so that halogen in the hydrogen-containing hydrocarbon halide is substituted by fluorine.

BACKGROUND OF THE INVENTION

Methods for producing hydrocarbon fluorides (fluorohydrocarbons) by reacting hydrogen-containing hydrocarbon halides (halohydrocarbons) with anhydrous hydrogen fluoride in a liquid phase using a stannic halide as a catalyst are described in U.S. Pat. Nos. 2,452,975 and 2,495,407 and Japanese Patent Publication No. 39086/72. In the method described in U.S. Pat. No. 2,452,975, a hydrogen-containing saturated hydrocarbon halide is reacted with anhydrous hydrogen fluoride in a liquid phase using stannic chloride as a catalyst; according to this patent, stannic chloride is milder in catalytic action than antimony halides which are common fluorination catalysts, and the formation of coke as a by-product is negligible when stannic chloride is used. In the method described in U.S. Pat. No. 2,495,407, a hydrogen-containing unsaturated hydrocarbon halide is reacted with anhydrous hydrogen fluoride using stannic chloride as a catalyst. In the method described in Japanese Patent Publication No. 39086/72, 1,1-difluoro-1-chloroethane is produced by reacting vinylidene chloride with hydrogen fluoride in the presence of stannic chloride; according to this patent, the formation of a by-product polymer is drastically reduced as compared with a method using antimony pentachloride as a catalyst, and since stannic chloride is less active to water than antimony pentachloride, the former can be reused as the catalyst if water content in the starting materials is low.

When a hydrogen-containing hydrocarbon halide such as 1,1,2-trichloroethane or 1,2-dichloro-1-fluoroethane is reacted with anhydrous hydrogen fluoride in a liquid phase using a stannic halide as a catalyst, higher boiling substances, oligomers or black precipitates are formed as by-products although their amounts are smaller than when an antimony halide is used as a catalyst. These by-products cause two major disadvantages: firstly, they reduce the selectivity for the end product; secondly, in industrial operations, equipment for removing or otherwise treating these by-products is necessary, rendering the overall manufacturing process complicated.

The terminology "higher boiling substances" means the compounds of fairly low molecular weights that are formed as a result of dimerization or trimerization of the hydrogen-containing hydrocarbon halide or its fluorine-substituted product. The "oligomers" are the products of further polymerization of such higher boiling substances. The "black precipitates" are those brown to black carbide-like substances which are not soluble either in the reaction solution formed upon completion of the fluorination or in water or acetone.

The present inventors found that the formation of higher boiling substances, oligomers or black precipitates occurred when a stannic halide was used as the sole catalyst for the fluorination of hydrogen-containing hydrocarbon halides. This phenomenon was particularly noticeable in the fluorination of 1,1,2-trichloroethane or 1,2-dichloro-1-fluoroethane. It is believed that the reason is as follows: when a hydrogen atom is present in the hydrocarbon halide, removal of hydrogen halides such as HCl or HF occurs during the reaction and the resulting dimerization or trimerization provides favorable conditions for the formation of higher boiling substances, oligomers or black precipitates.

The present inventors also found that when a hydrocarbon halide was reacted with anhydrous hydrogen fluoride in a liquid state using stannic chloride as a catalyst, the reaction mixture remained in a liquid form in the initial stage of reaction, but as the reaction proceeded, tin-derived tar started to form. The hydrocarbon halide and the anhydrous hydrogen fluoride were not completely miscible and formed two-liquid phases. The stannic chloride was liquid and was not soluble in the anhydrous hydrogen fluoride but soluble in the hydrocarbon halide and, as a result, the reaction solution was composed of two liquid phases. However, $SnCl_2F_2$ and $SnF_4$ which were fluorinated products of stannic chloride ($SnCl_4$) were solid and were not soluble in either the anhydrous hydrogen fluoride or the hydrocarbon halide. As the reaction proceeds, the stannic chloride is also fluorinated. It is believed that the resulting fluorination products (e.g. $SnCl_2F_2$ and $SnF_4$) combine with a certain amount of the hydrocarbon halide to form a tar-like substance. This tin-derived tar clogs nozzles in the reactor or pipes and is a great obstacle to the purpose of carrying out the reaction in a continuous manner. Even if the catalyst is selected from stannic halides other than stannic chloride, stannic oxyhalides and organotin compounds, a similar tin-derived tar would be formed as the reaction proceeds.

It has heretofore been understood that oxygen-containing organic compounds and water are highly deleterious to the fluorination of hydrocarbons in the presence of metal halides, and these compounds and water are thoroughly removed from the starting material before reaction is started, as described in, for example, U.S. Pat. No. 2,005,708 and Yuki Fusso Kagaku (Chemistry of Organic Fluorine Compounds), Vol. I, p. 247, published by Gihodo Co. (1970). As a matter of fact, it was confirmed that fluorination catalyzed by antimony pentachloride or titanium tetrachloride was appreciably impeded by the addition of oxygen-containing organic compounds or water.

SUMMARY OF THE INVENTION

An object of the present invention is to provide an industrially useful process for producing a hydrocarbon fluoride with minimum formation of by-products such as high-boiling point substances, oligomers and black precipitates while maximizing the selectivity for the end product.

Another object of the present invention is to provide an industrially useful process for producing a hydrocarbon fluoride with minimum formation of tin-derived tar.

As a result of extensive study to attain these objects, it has surprisingly been found that when a stannic halide, a stannic oxyhalide or an organotin compound is positively used in admixture with an oxygen-containing compound and/or a nitrogen-containing compound in fluorination of hydrogen-containing hydrocarbon halides with anhydrous hydrogen fluoride, reaction occurs between the tin compound, the oxygen-containing compound and/or nitrogen-containing compound and the anhydrous hydrogen fluoride, thereby producing a new tin compound which is entirely dissimilar not only from the tin compound but also from its fluorimated compound such as $SnCl_2F_2$ or $SnF_4$ and which is soluble in the anhydrous hydrogen fluoride and even when the reaction proceeds, so that not only does the reaction proceed unimpeded but also the formation of by-products such as higher boiling substances, oligomers and black precipitates is drastically reduced while the selectivity for the end product is improved.

Thus, the present invention is directed to a process for producing a hydrocarbon fluoride comprising reacting a hydrogen-containing hydrocarbon halide with anhydrous hydrogen fluoride in a liquid phase in the presence of a reaction product of (i) at least one of (a) an oxygen-containing compound selected from the group consisting of $H_2O$, $H_2O_2$ and an oxygen-containing organic compound, and (b) a nitrogen-containing compound selected from the group consisting of $NH_3$ and a nitrogen-containing organic compound (ii) a tin compound selected from the group consisting of a stannic halide, a stannic oxyhalide and an organotin compound, and (iii) anhydrous hydrogen fluoride.

BRIEF DESCRIPTION OF THE DRAWINGS

FIG. 3 is a gas chromatograph of an organic phase containing dimers obtained in Comparative Example 1.

FIG. 4 is a gas chromatograph of the organic phase containing dimers obtained in Example 1.

DETAILED DESCRIPTION OF THE INVENTION

Figure 1:
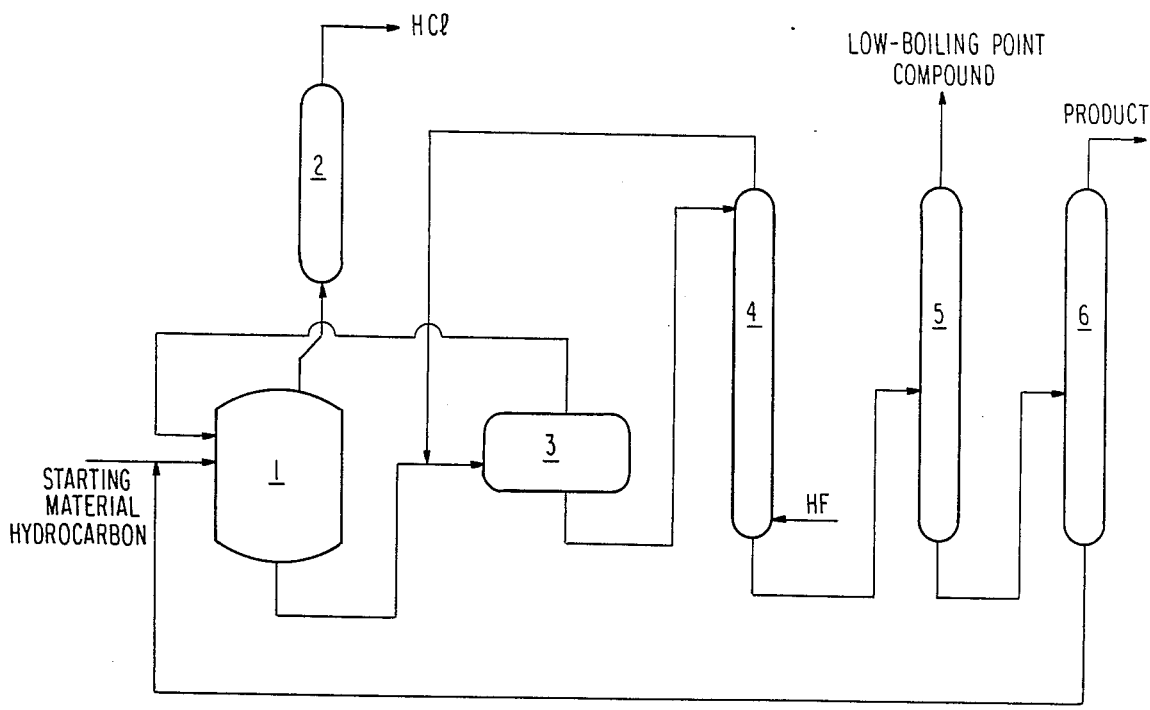
FIG. 1 shows a flowsheet of the liquid withdrawing process for performing the method of the present invention in a continuous manner.

The reaction product of (i) the oxygen-containing compound and/or the nitrogen-containing compound, (ii) the tin compound and (iii) the anhydrous hydrogen fluoride is a novel tin catalyst that forms as a result of reaction between these three compounds. One important feature of this novel tin catalyst is that it dissolves in the anhydrous hydrogen fluoride. This novel tin catalyst will result only when the aforementioned three reactants exist and will not form if only two of them are combined such as the combination of (i) the oxygen-containing compound and/or the nitrogen-containing compound and (ii) the tin compound, or of (i) the oxygen-containing compound and/or the nitrogen-containing compound and (iii) the anhydrous hydrogen fluoride, or of (ii) the tin compound and (iii) the anhydrous hydrogen fluoride. It should, however, be noted that if the tin compound is a stannic oxyhalide, it may simply be combined with the anhydrous hydrogen fluoride to form the novel tin catalyst.

The oxygen-containing compounds which can be used as the component (i) in the present invention includes $H_2O$, $H_2O_2$ and an oxygen-containing organic compound such as alcohols, ketones, carboxylic acids, aldehydes, ethers, esters and epoxy compounds. The oxygen-containing organic compounds may contain two or more groups, which may be the same or different, selected from hydroxyl, carbonyl, carboxyl, ester, ether and epoxy groups. More specific examples of these oxygen-containing organic compounds include methyl alcohol, ethyl alcohol, propyl alcohol, butyl alcohol, ethylene glycol, acetone, methyl ethyl ketone, formic acid, acetic acid, propionic acid, formaldehyde, butylaldehyde, methyl ether, ethyl ether, tetrahydrofuran, 1,4-dioxane, ethylene glycol monoethyl ether. Alcohols (particularly monohydric alcohols) and water are preferably used as the oxygen-containing compounds.

The nitrogen-containing compounds which can be used as the component (i) in the present invention include $NH_3$ and a nitrogen-containing organic compound such as amines. Examples of amine include pyridine, triethylamine, sec-butylamine, hexamethylenediamine, aniline, toluidine and triethanolamine, with pyridine and triethylamine being preferred.

The oxygen-containing compounds and the nitrogen-containing compounds may be used either singly or in admixture.

The tin compounds (ii) used in the present invention include stannic halides such as $SnCl_4$, $SnF_4$ $SnBr_4$, and $SnCl_xF_{4-x}$ ($0<x<4$) of the type which results from $SnCl_4$ and HF; stannic oxyhalides such as $SnCl_2O$, $SnF_2O$ and SnClFO; and organotin compounds wherein Sn is bonded to C, such as tetramethyl tin, oxydiethyl tin and dichlorodimethyl tin. The oxygen-containing compound, nitrogen-containing compound and the tin compound which are necessary for forming the novel tin catalyst may be used either singly or in admixture so long as they are selected to provide both O and/or N and Sn. In the combination of the tin compound and water, they may be added separately or as in the form of hydrates of the tin compound such as $SnCl_4.2H_2O$ and $SnCl_4.5H_2O$. Of these tin compounds, stannic halides are preferred from an economic viewpoint, and stannic chloride is more preferably used.

Two methods are available for carrying out the reaction between the hydrogen-containing hydrocarbon halide and the anhydrous hydrogen fluoride using the novel tin catalyst (i.e., the reaction product of the components (i), (ii) and (iii): in the first method, the novel tin catalyst is formed by preliminary reaction between the oxygen-containing compound and/or the nitrogen-containing compound, the tin compound and the anhydrous hydrogen fluoride, and thereafter, the hydrogen-containing hydrocarbon halide is reacted with the anhydrous hydrogen fluoride in the presence of the novel tin catalyst; alternatively, reaction may be initiated by simultaneous addition of the oxygen-containing compound and/or the nitrogen-containing compound, the tin compound, the anhydrous hydrogen fluoride and the hydrogen-containing hydrocarbon halide. In the latter method, the anhydrous hydrogen fluoride may be used both for producing the novel tin catalyst and as a reactant with the hydrogen-containing hydrocarbon halide.

In the formation of the novel tin catalyst by the reaction between the oxygen-containing compound, the tin compound and the anhydrous hydrogen fluoride, the molar ratio of oxygen atoms to tin atoms (O/Sn) in the novel tin catalyst is from 0.2/1 to 2/1 and preferably from 0.5/1 to 1.5/1. If it exceeds 2/1, the rate of reaction sharply decreases. This limitation on the molar ratio of oxygen atoms to tin atoms is that of the atoms within the novel tin catalyst, so if an initial addition of the oxygen-containing compound is not thoroughly reacted with the tin compound or the anhydrous hydrogen fluoride, the oxygen-containing compound may additionally be supplied.

The novel tin catalyst in accordance with the present invention has the following characteristic differences from stannic halide such as $SnCl_2$, $SnCl_2F_2$ and $SnF_4$.

The first major difference concerns solubility in solvents: $SnCl_4$ is soluble in non-polar solvents such as 1,1,2-trichloroethane and chloroform, but both $SnCl_2F_2$ and $SnF_4$ remain solid and insoluble in these solvents. The novel tin catalyst is also insoluble in non-polar solvents and forms a two-liquid phase, in some cases, accompanied by partial precipitation.

All of the four compounds ($SnCl_4$, $SnCl_2F_2$, $SnF_4$ and the novel tin catalyst) are soluble in polar solvents such as methanol and acetone. In view of great amount of heat that is generated, it is believed that these compounds dissolve in methanol and acetone by coordination of the Sn atom with these solvents.

None of the stannic halides are soluble in polar anhydrous hydrogen fluoride, but the novel tin catalyst is completely soluble.

$SnCl_4$ is reacted with HF to form a precipitate. A $^{119}$Sn-NMR spectrum of this precipitate is substantially the same as that of a mixture of $SnCl_4$, $SnF_4$, $SnCl_2F_2$ and $SnClF_3$. On the other hand, a $^{119}$Sn-NMR spectrum of the novel tin catalyst greatly differs from these spectra in terms of both chemical shifts and coupling constants. Therefore, the $^{119}$Sn-NMR spectra support the fact that the novel tin catalyst is quite dissimilar from such stannic halides as $SnCl_4$, $SnCl_2F_2$ and $SnF_4$. (It should, however, be mentioned that $CD_3OD$ used as a solvent for $^{119}$Sn-NMR spectrometry in place of non-polar solvents that did not dissolve the novel tin catalyst might have coordinated with the stannic halides or novel tin catalyst to cause variations from the structures they would initially assume within the anhydrous hydrogen fluoride.

A GC-mass spectrum of the novel tin catalyst that was produced from sec-butyl alcohol, $SnCl_4$, and HF revealed differences in atomic weight between Sn, F and O. This result suggests the presence of O in the molecule of the novel tin catalyst in addition to Sn, F and Cl. Here again it should be mentioned that the ultra-high vacuum and high temperature conditions used in GC-mass spectrometry might have caused changes in the initial structure of the catalyst.

The terminology "hydrogen-containing hydrocarbon halide" may include any hydrocarbon halide that contains hydrogen in the molecule. Among hydrogen-containing hydrocarbon halides having two carbon atoms bonded by a single bond, those represented by formulae (I) and (II) are preferred:

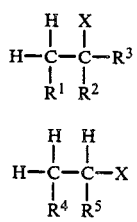

wherein X represents a halogen atom other than F; $R^1$, $R^4$ and $R^5$ each represents a hydrogen atom, a halogen atom, a hydrocarbon group, or a hydrocarbon halide group; and $R^2$ and $R^3$ each represents a halogen atom, a hydrocarbon group, or a hydrocarbon halide group.

Illustrative examples include 1,1,1-trichloroethane, 1,1,1,2-tetrachloroethane, 1,1,2-trichloroethane and 1,2-dichloro-1-fluoroethane. Among hydrogen-containing hydrocarbon halides having two carbon atoms bonded together by a double bond, those represented by formulae (III), (IV-1) and (IV-2) are preferred:

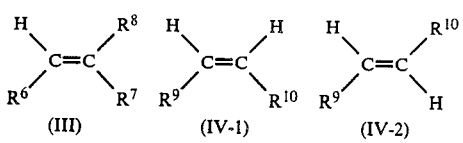

wherein $R^6$, $R^9$ and $R^{10}$ each represents a hydrogen atom, a halogen atom a hydrocarbon group, or a hydrocarbon halide group; and $R^7$ and $R^8$ each represents a halogen atom, a hydrocarbon group, or a hydrocarbon halide group; provided that $R^7$ and $R^8$ are not hydrogen groups at the same time when $R^6$ is a hydrogen atom or a hydrocarbon group, and $R^9$ and $R^{10}$ are not a hydrogen atom and/or a hydrocarbon group at the same time. Illustrative examples include 1,1-dichloroethylene, trichloroethylene and 1,2-dichloroethylene.

Of these hydrogen-containing hydrocarbon halides, those of formulae (II), (IV-1) and (IV-2) are more preferred. Particularly good results are obtained by using 1,1,2-trichloroethane, 1,2-dichloro-1-fluoroethane or 1,2-dichloroethylene. Needless to say, hydrocarbon halides having three or more carbon atoms may be employed if they contain hydrogen, and the halogen may be bromine or iodine.

When halides other than stannic halides, such as, for example, antimony pentachloride and titanium tetrachloride are used to produce a hydrocarbon fluoride by reacting the hydrogen-containing hydrocarbon halide and anhydrous hydrogen fluoride, by-products such as higher boiling substances, oligomers and black precipitates forms in even greater amounts than when the reaction is performed with the stannic halide being used as the sole catalyst. If an oxygen-containing compound (e.g., sec-butyl alcohol) or a nitrogen-containing compound is used in combination with antimony pentachloride or titanium tetrachloride to minimize the formation of such by-products, the catalytic activity of these metal halides is lost as a result of their reaction with, for example, sec-butyl alcohol, and the conversion of the hydrogen-containing hydrocarbon halide is extremely reduced. On the other hand, if a stannic halide such as stannic chloride is used in admixture with an oxygen-containing compound (e.g., sec-butyl alcohol or water) or a nitrogen-containing compound, the stannic chloride will also react with sec-butyl alcohol or water within the anhydrous hydrogen fluoride to form the novel tin catalyst, but the catalytic activity of this novel tin catalyst is kept high enough to avoid any substantial drop in the conversion of the hydrogen-containing hydrocarbon halide. Since sec-butyl alcohol or water has entered into reaction with the stannic chloride, these oxygen-containing compounds are quite dissimilar in concept from ordinary solvents.

The hydrogen-containing hydrocarbon halide may be reacted with the anhydrous hydrogen fluoride in the presence of the aforementioned novel tin catalyst under the conditions commonly employed in the current practice of liquid-phase fluorination with anhydrous hydrogen fluoride. For example, when the starting material is 1,1,2-trichloroethane or 1,2-dichloro-1-fluoroethane, the reaction temperature is generally from 50° to 200° C., preferably from 70° to 150° C. and the reaction pressure is generally from 3 to 30 kg/cm$^2$G, preferably from 5 to 20 kg/cm$^2$G. If necessary, the by-product hydrogen chloride may be withdrawn from the reaction system.

It is preferred that the molar ratio of total fluorine atoms (i.e., F in the anhydrous hydrogen fluoride plus F in the novel tin catalyst to tin atoms (F/Sn) in the reaction liquid be from 6/1 to 100/1 and preferably from 9/1 to 50/1. If it is less than 6/1, the reaction rate is decreased. On the other hand, if the molar ratio of F/Sn is more than 100/1, the concentration of the tin compound in the HF phase is low, resulting in decrease of the reaction rate. The molar ratio of Sn to the hydrogen-containing hydrocarbon halide is generally 0.05/1 or more and preferably 0.07/1 or more. If the ratio is less than 0.05/1, the reaction rate is also decreased.

Various processes may be employed for carrying out the reaction continuously: one may be referred to as the "liquid withdrawing process" wherein the reaction mixture is separated into the HF phase containing the novel tin catalyst and the organic phase containing the product, and the product is recovered from this organic phase, utilizing the property of the novel tin catalyst that is soluble in the anhydrous hydrogen fluoride but is sparingly soluble in the hydrogen-containing hydrocarbon fluoride halide; and the other process may be designated as the "vapor withdrawing process", wherein the product is recovered as vapor without withdrawing the catalyst or higher boiling substances, utilizing advantage of the present invention that undesired by-products such as higher boiling substances, oligomers, black precipitates and tin-derived tar are not substantially produced during the reaction.

Figure 2:
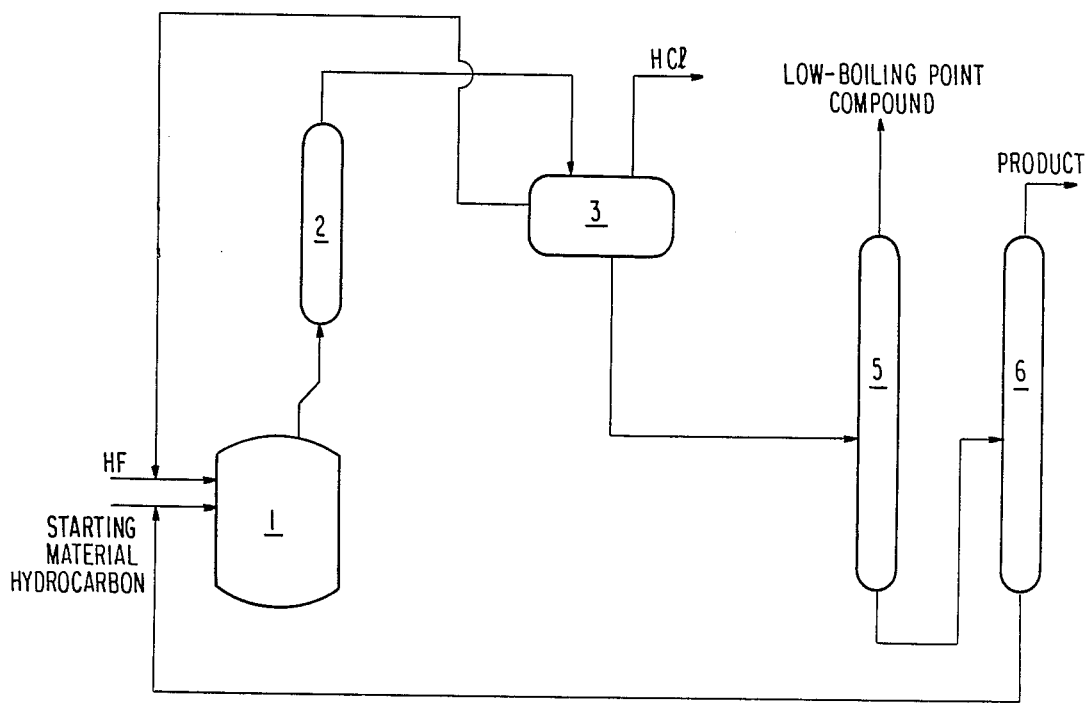
FIG. 2 shows a flowsheet of the vapor withdrawing process for performing the method of the present invention in a continuous manner.

Detailed procedures of these two continuous processes are hereunder described, with reference to FIGS. 1 and 2.

FIG. 1 shows a flowsheet for the liquid withdrawing process. In reactor 1, a hydrogen-containing hydrocarbon halide is reacted with anhydrous hydrogen fluoride in the presence of the novel tin catalyst. The by-product hydrogen halide (e.g., hydrogen chloride) is withdrawn from a condenser (or distillation column) 2 as a vapor after removing the entrained hydrogen fluoride and hydrocarbon by condensation. The condensed hydrogen fluoride and hydrocarbon are recycled to the reactor. The content of the reactor is a two-liquid phase composed of the organic phase and the HF phase. This two-liquid phase is directly withdrawn from the reactor and fed to a decanter 3 for separation purposes. The novel tin catalyst is principally contained in the HF phase, which therefore is recycled to the reactor. The specific gravity of the HF phase varies with the Sn concentration. If the Sn concentration is high, the HF phase has a higher specific gravity than the organic phase and lies under the orgenic phase in the decanter. In the process shown in FIG. 1, the Sn concentration is adjusted to a relatively low level so that the HF phase lies above the organic phase.

The organic phase separated from the HF phase in the decanter still contains a small amount of the novel tin catalyst, which may be recovered by extraction with anhydrous hydrogen fluoride in an extractor column 4. The organic phase that leaves the extractor column and which is substantially free from the novel tin catalyst may be purified by customary distillation procedures. For example, fractions of low boiling points are separated from the organic phase by a distillation column 5, and the remainder is fed to another distillation column 6 to separate the product from the starting material having a higher boiling point than that of the product. The starting material, or the hydrogen-containing hydrocarbon halide, that has been separated from the product is recycled to the reactor.

In the liquid withdrawing process described above, Sn-containing tar that cause troubles forms at the bottom of the distillation columns unless the novel tin catalyst in the organic phase is thoroughly recovered by extraction with anhydrous hydrogen fluoride. However, in the reactor, decanter and extractor column where the anhydrous hydrogen fluoride is present, the formation of such Sn-containing tar is negligible since the novel tin catalyst is soluble in the anhydrous hydrogen fluoride.

FIG. 2 shows a flowsheet for the vapor withdrawing process, wherein hydrogen fluoride and the product are withdrawn in the form of vapors that entrain the by-product hydrogen halide (e.g., hydrogen chloride gas) and are separated into the HF phase and the organic phase in a decanter 3. Any entrained starting material (i.e., hydrogen-containing hydrocarbon halide) may be separated from the product in a distillation column 2 immediately above a reactor 1 and recycled to the reactor.

The HF phase separated from the organic phase in the decanter is also recycled to the reactor, and the recycled HF phase is substantially free from the novel tin catalyst. The organic phase separated from the HF phase in the decanter is principally composed of the product and may be purified by customary distillation procedures as described above. The bottoms composed mainly of the starting material (i.e., hydrogen-containing hydrocarbon halide) are recycled to the reactor.

In this vapor withdrawing process, no liquid is withdrawn from the reactor and, therefore, if any of the by-products such as higher boiling substances, oligomers, black precipitates and tin-derived tar form, liquid must be withdrawn from the reactor either continuously or batchwise for treating such by-products. However, the formation of such by-products is substantially absent from the reaction that is carried out in the presence of the novel tin catalyst, and an extended continuous operation is realized without withdrawing any liquid from the reactor.

The following examples are provided for the purpose of further illustrating the present invention. The analytical methods and apparatus used in the examples are identified below.

Elemental analysis: Sn: atomic absorption spectrometer (Model 170-10 of Hitachi, Ltd.); F: ion electrode (Model F-125 of Toa Electronics Ltd.); ion meter (Model 1M 20E of Toa Electronics Ltd.); Cl: ion electrode (Model CL-135 of Toa Electronics Ltd.); ion meter (Model 1M 1E of Toa Electronics Ltd.).

Gas chromatography: Model GC-3BT of Shimadzu Seisakusho, Ltd. with column packing of Apiezon Grease; Model GC-3BF of Shimadzu Seisakusho, Ltd. with column packing of Squalane.

NMR: Model GX-400 of Jeol, Ltd.

GC-MS: Model JMS-D300 of Jeol, Ltd.

EXAMPLE 1

A 200-ml reactor made of Hastelloy C was charged with 66.7 g (0.5 mole) of 1,1,2-trichloroethane, 23 g (1.15 moles) of anhydrous hydrogen fluoride, 19.5 g (0.075 mole) of stannic chloride and 2.07 g (0.045 mole) of ethyl alcohol. The reactor was equipped with a stirrer, a condenser, a thermometer and a pressure gage, with a pressure regulating valve disposed at the outlet of the condenser. A coolant (about −10° C.) was caused to flow through the condenser so that hydrogen fluoride accompanying the by-product hydrogen chloride was condensed and returned to the reactor.

The reactor was placed in a 300W mantle heater and the temperature in the reactor was elevated. When the pressure in the reactor reached 10 kg/cm²G, the by-product hydrogen chloride was begun to be withdrawn and the pressure was maintained throughout the reaction. No special provision was made to control the reaction temperature, but it was substantially held at a constant level between 95° and 115° C. Three hours after the start of temperature elevation, the heater was turned off and the reactor was cooled. Thereafter, the reaction solution was recovered and washed with water to be separated into the organic phase and the aqueous phase. Gas chromatographic analysis of the organic phase was conducted to determine the conversion of 1,1,2-trichloroethane and the yields of 1,2-dichloro-1-fluoroethane and 2-chloro-1,1-difluoroethane. The yield was the number of moles of the end product divided by the number of moles of the charged 1,1,2-trichloroethane. Further, the concentrations of dimers in the organic phase were determined by gas chromatography. The results of Example 1 are shown in Table 1.

EXAMPLES 2 TO 7 AND COMPARATIVE EXAMPLE 1

Fluorination was conducted as in Example 1 except that the ethyl alcohol as the oxygen-containing compound was replaced by iso-propyl alcohol (Ex. 2), sec-butyl alcohol (Ex. 3), tert-butyl alcohol (Ex. 4), acetone (Ex. 5), acetic acid (Ex. 6) and water (Ex. 7). The results are shown in Table 1 together with the data for Comparative Example 1 wherein reaction was carried out in the same manner as in Example 1 except that no ethyl alcohol was added.

The organic phases containing dimers obtained in Comparative Example 1 and Example 1 were analyzed by gas chromatography and the results are shown in FIGS. 3 and 4, respectively. The dimers are indicated by peaks (1) to (4) in FIG. 3 and peaks (1) and (2) in FIG. 4. GC-MS and NMR spectra revealed that each of (1) and (2) was a diastereomer of $CH_2Cl-CHCl-CHCl-CHClF$ and each of (3) and (4) was a diastereomer of $CH_2Cl-CHCl-CHCl-CHCl_2$. If the concentration of these dimers is high, the amounts of oligomers and black precipitates that are products of further polymerization of the dimers also increase.

TABLE 1

|  | Ex. 1 | Ex. 2 | Ex. 3 | Ex. 4 | Ex. 5 | Ex. 6 | Ex. 7 | Comp. Ex. 1 |
|---|---|---|---|---|---|---|---|---|
| O-Containing Compound | Ethyl Alcohol | Iso-Propyl Alcohol | Sec-Butyl Alcohol | Tert-Butyl Alcohol | Acetone | Acetic Acid | H₂O | None |
| O-Containing Compound/SnCl₄ (mole/mole) | 0.6 | 0.6 | 0.6 | 0.6 | 0.6 | 0.6 | 0.6 | 0 |
| Conversion (%) | 88 | 89 | 91 | 84 | 83 | 89 | 88 | 96 |
| Yeild (%): |  |  |  |  |  |  |  |  |
| 1,2-Dichloro-1-fluoroethane | 49 | 69 | 68 | 64 | 65 | 59 | 52 | 54 |
| 2-Chloro-1,1-difluoroethane | 25 | 17 | 15 | 10 | 7 | 13 | 21 | 15 |
| Total | 74 | 86 | 83 | 74 | 72 | 72 | 73 | 69 |
| Concentration of Dimers in Organic Phase (wt %) | 0.31 | 0.45 | 0.26 | 0.15 | 0.11 | 0.27 | 0.32 | 3.0 |

EXAMPLE 8

A 1,000-ml reactor made of Hastelloy C was charged with 667 g (5.0 moles) of 1,1,2-trichloroethane, 230 g (11.5 moles) of anhydrous hydrogen fluoride, 195 g (0.75 mole) of stannic chloride and 33 g (0.45 mole) of sec-butyl alcohol. Like the 200-ml reactor used in Examples 1 to 7, the reactor was equipped with a stirrer, a condenser, a thermometer and a pressure gage. This reactor was immersed in an oil bath preheated at 200° C. The bath was equipped with a thermometer and two 500 W heaters and the temperature in the oil bath was maintained at 200° C. throughout the reaction. When the pressure in the reactor in the oil bath reached 10 kg/cm²G, the by-product hydrogen chloride was begun to be withdrawn and the pressure value of 10 kg/cm²G was maintained in the subsequent period of reaction. After the pressure in the reactor leveled off at 10 kg/cm²G, the temperature of the reaction solution also leveled off at between 96° C. and 120° C. Three hours after the start of the reaction, the heater was turned off and the reactor was allowed to cool. The reaction solution was then recovered and analyses were made to determine the conversion of 1,1,2-trichloroethane and the yields of the products. The concentration of dimers in the organic phase and the amount of a black precipitate formed in the reaction solution were also determined. The results are shown in Table 2.

EXAMPLE 9 AND COMPARATIVE EXAMPLE 2

The procedures of Example 8 were repeated except that the amount of sec-butyl alcohol was increased to 56 g (0.75 mole). The results are shown in Table 2 together with the data for Comparative Example 2 wherein sec-butyl alcohol was not added.

TABLE 2

|  | Ex. 8 | Ex. 9 | Comp. Ex. 2 |
|---|---|---|---|
| Amount of Sec-Butyl Alcohol (g) | 33 | 56 | 0 |
| Sec-Butyl Alcohol/SnCl₄ (mole/mole) | 0.6 | 1.0 | 0 |
| Reaction Time (hr) | 3 | 3 | 3 |
| Conversion (%) | 77 | 61 | 72 |
| Yield (%): |  |  |  |

TABLE 2-continued

|  | Ex. 8 | Ex. 9 | Comp. Ex. 2 |
|---|---|---|---|
| 1,2-Dichloro-1-fluoroethane | 62 | 56 | 57 |
| 2-Chloro-1,1-difluoroethane | 13 | 4 | 8 |
| Total | 75 | 60 | 65 |
| Concentration of Dimers in Organic Phase (wt %) | 0.16 | 0.19 | 0.70 |
| Amount of Black Precipitate (g) | ≈0 | ≈0 | 0.5 |

EXAMPLE 10 AND COMPARATIVE EXAMPLE 3

The procedures of Example 8 were repeated except that 1,2-dichloro-1-fluoroethane was used as the starting material. The results are shown in Table 3 together with the data for Comparative Example 3 wherein sec-butyl alcohol was not added and the reaction period was shortened to 1.5 hours. In spite of the change in starting material used, the by-product dimers were identical to those formed in Examples 1 to 9.

TABLE 3

|  | Ex. 10 | Comp. Ex. 3 |
|---|---|---|
| Amount of Sec-Butyl Alcohol (g) | 56 | 0 |
| Sec-Butyl Alcohol/SnCl$_4$ (mole/mole) | 1.0 | 0 |
| Reaction Time (hr) | 3 | 1.5 |
| Conversion (%) | 28 | 47 |
| Yield (%): |  |  |
| 2-Chloro-1-difluoroethane | 19 | 8 |
| 1,1,2-Trichloroethane | 3 | 13 |
| Total | 22 | 21 |
| Concentration of Dimers in Organic Phase (wt %) | 0.26 | 2.8 |
| Amount of Black Precipitate (g) | ≈0 (not detected) | 2.9 |

EXAMPLE 11 AND COMPARATIVE EXAMPLE 4

A 1,000-ml reactor made of Hastelloy C equipped with a stirrer, a condenser, a thermometer and a pressure gage was used. This reactor was also equipped with a nozzle and valve at the bottom so that the reaction solution obtained at completion of the reaction could be withdrawn after cooling. A 1.5 kW mantle heater was used as means for heating the reactor.

This reactor was charged with 587 g (4.4 moles) of 1,1,2-trichloroethane, 308 g (15.4 moles) of anhydrous hydrogen fluoride, 172 g (0.66 mole) of stannic chloride and 48.9 g (0.66 mole) of sec-butyl alcohol. The voltage to the mantle heater was adjustable by an variable transformer and held at 70 volts throughout the reaction. When the pressure in the reactor reached 10 kg/cm$^2$G, the by-product hydrogen chloride was begun to be withdrawn so that this pressure value was maintained in the subsequent stage of reaction. Three hours after the start of the reaction, the heater was turned off and the reactor was cooled. The reaction solution was then recovered from the reactor through the bottom nozzle. It consisted of two liquid phases, HF and organic phases, and no detectable tin-derived tar was present.

The concentration of Sn in the organic phase and HF phase were 2.1 wt% and 24.8 wt%, respectively, suggesting that the greater part of the Sn present dissolved in the HF phase. The concentration of dimers in the organic phase was 0.13 wt%, which was much lower than 2.3 wt% for the concentration in Comparative Example 4 wherein no sec-butyl alcohol was added. The results are shown in Table 4.

EXAMPLES 12 TO 16

The procedures of Example 11 were repeated except that the amounts of anhydrous hydrogen fluoride, stannic chloride and sec-butyl alcohol were changed to the values indicated in Table 4. The results are also shown in Table 4.

TABLE 4

|  | Ex. 11 | Ex. 12 | Ex. 13 | Ex. 14 | Ex. 15 | Ex. 16 | Comp. Ex. 4 |
|---|---|---|---|---|---|---|---|
| Charged amounts (mole): |  |  |  |  |  |  |  |
| 1,1,2-trichloroethane | 4.4 | 4.4 | 4.4 | 4.4 | 4.4 | 4.4 | 4.4 |
| anhydrous hydrogen fluoride | 15.4 | 15.4 | 10.2 | 22.0 | 15.4 | 15.4 | 15.4 |
| SnCl$_4$ | 0.66 | 0.66 | 0.66 | 0.66 | 0.33 | 1.32 | 0.66 |
| sec-butyl alcohol | 0.66 | 0.66 | 0.66 | 0.66 | 0.33 | 1.32 | 0 |
| Voltage to mantle heater (V) | 70 | 50 | 70 | 70 | 70 | 70 | 70 |
| Reaction pressure (kg/cm$^2$G) | 10 | 10 | 10 | 10 | 10 | 10 | 10 |
| Reaction temperature (°C.) | 99~102 | 99~101 | 99~114 | 99~100 | 99~102 | 99~100 | 95~101 |
| HF phase: | lower layer | lower layer | lower layer | lower layer | upper layer | lower layer | upper layer |
| Cl$^-$ (wt %) | 2.8 | 4.3 | 4.6 | 3.3 | 1.8 | 5.4 | 1.2 |
| F$^-$ (wt %) | 35.1 | 59.4 | 41.9 | 53.6 | 65.0 | 39.9 | 90.0 |
| Sn (wt %) | 24.8 | 21.6 | 33.3 | 17.4 | 12.6 | 35.4 | 0.6 |
| Organic matter (wt %) | ≈0 | ≈0 | ≈0 | ≈0 | ≈0 | ≈0 | ≈0 |
| balance | 37.3 | 14.7 | 20.2 | 25.7 | 20.6 | 19.3 | 8.2 |
| Organic phase: | upper layer | upper layer | upper layer | upper layer | lower layer | upper layer | lower layer |
| Cl$^-$ (wt %) | 1.2 | 2.2 | 1.3 | 0.4 | 0.2 | 2.2 | 7.8 |
| F$^-$ (wt %) | 2.9 | 2.8 | 2.4 | 2.2 | 1.0 | 4.2 | 3.7 |
| Sn (wt %) | 2.1 | 2.9 | 1.9 | 0.3 | 0.1 | 4.0 | 10.3 |
| balance (predominantly organic) | 93.8 | 92.1 | 94.4 | 97.1 | 98.7 | 89.6 | 78.2 |
| In organic matter (wt %): |  |  |  |  |  |  |  |
| 1,1,2-trichloroethane | 27.4 | 69.9 | 47.3 | 23.8 | 81.6 | 34.9 | 22.7 |
| 1,2-dichloro-1-fluoroethane | 65.8 | 29.2 | 49.1 | 67.3 | 18.3 | 57.5 | 62.2 |
| 2-chloro-1,1-difluoroethane | 6.3 | 0.5 | 3.2 | 8.0 | 0.1 | 6.4 | 12.7 |
| dimers | 0.13 | 0.01 | 0.01 | 0.34 | 0.00 | 0.04 | 2.3 |
| Sn-derived tar | negligible | negligible | negligible | negligible | negligible | negligible | positive |

EXAMPLE 17

The procedures of Example 11 were repeated except that 48.9 g (0.66 mole) of sec-butyl alcohol was replaced by 11.9 g (0.66 mole) of water. As in Example 11, the reaction solution separated into two liquid phases, HF and organic phases, and no detectable tin-derived tar occurred. The concentrations of Sn in the organic phase and HF phase were 1.2 wt% and 28.8 wt%, respectively, suggesting that the greater part of the Sn present dissolved in the HF phase. The concentration of dimers in the organic phase was 0.36 wt%, which was much lower than 2.3 wt% for the concentration in Comparative Example 4 wherein stannic chloride was used as the sole catalyst. The results are shown in Table 5.

EXAMPLE 18

The procedures of Example 17 were repeated except that the reaction pressure was decreased to 7.5 kg/cm$^2$G. The results are shown in Table 5.

EXAMPLES 19, 20 AND 21

The procedures of Example 17 were repeated except that the amount of water was changed to the values shown in Table 5. The results are also shown in Table 5.

withdrawn after cooling. A 500 W mantle heater was used as means for heating the reactor.

This reactor was charged with 133 g (1.0 mole) of 1,1,2-trichloroethane, 40.0 g (2.0 moles) of anhydrous hydrogen fluoride, 39.1 g (0.15 mole) of stannic chloride and 10.8 g (0.15 mole) of butyl aldehyde. The voltage supplied to the mantle heater was adjustable by an variable transformer and held at 65 volts throughout the reaction. When the pressure in the reactor reached 10 kg/cm$^2$G, the by-product hydrogen chloride was begun to be withdrawn so that this pressure value was maintained in the subsequent stage of reaction. Three hours after the start of the reaction, the heater was turned off and the reactor was cooled. The reaction solution was then recovered from the reactor through the bottom nozzle. It consisted of two liquid phases, HF and organic phases, and no detectable tin-derived tar was present.

The concentrations of Sn in the organic phase and HF phase were 2.0 wt% and 24.7 wt%, respectively, suggesting that the greater part of the Sn present dissolved in the HF phase. The concentration of dimers in the organic phase was 0.00 wt%, which was much lower than 0.79 wt% for the concentration in Comparative Example 5 where no butyl aldehyde was added. The results are shown in Table 6.

TABLE 5

|  | Ex. 17 | Ex. 18 | Ex. 19 | Ex. 20 | Ex. 21 |
| --- | --- | --- | --- | --- | --- |
| Charged amounts (mole): |  |  |  |  |  |
| 1,1,2-trichloroethane | 4.4 | 4.4 | 4.4 | 4.4 | 4.4 |
| anhydrous hydrogen fluoride | 15.4 | 15.4 | 15.4 | 15.4 | 15.4 |
| SnCl$_4$ | 0.66 | 0.66 | 0.66 | 0.66 | 0.66 |
| H$_2$O | 0.66 | 0.66 | 0.69 | 0.99 | 1.32 |
| Voltage to mantle heater (V) | 70 | 70 | 70 | 70 | 70 |
| Reaction pressure (kg/cm$^2$G) | 10 | 7.5 | 10 | 10 | 10~8 |
| Reaction temperature (°C.) | 97~99 | 87~89 | 97~104 | 99~102 | 80~105 |
| HF phase: | lower layer | lower layer | lower layer | lower layer | lower layer |
| Cl$^-$ (wt %) | 5.5 | 4.9 | 5.0 | 3.6 | 1.3 |
| F$^-$ (wt %) | 54.9 | 58.6 | 61.8 | 63.0 | 71.3 |
| Sn(wt %) | 28.8 | 28.3 | 26.5 | 28.4 | 20.8 |
| Organic matter (wt %) | ≈0 | ≈0 | ≈0 | ≈0 | ≈0 |
| balance | 10.8 | 8.2 | 6.7 | 5.0 | 6.6 |
| Organic phase: | upper layer | upper layer | upper layer | upper layer | upper layer |
| Cl$^-$ (wt %) | 1.6 | 1.0 | 1.5 | 0.3 | 0.1 |
| F$^-$ (wt %) | 1.4 | 1.3 | 1.8 | 0.7 | 0.6 |
| Sn (wt %) | 1.2 | 0.8 | 1.8 | 0.3 | 0.1 |
| balance (predominantly organic) | 95.8 | 96.9 | 94.9 | 98.7 | 99.2 |
| In organic matter (wt %): |  |  |  |  |  |
| 1,1,2-trichloroethane | 19.8 | 25.1 | 22.9 | 47.6 | 87.9 |
| 1,2-dichloro-1-fluoroethane | 64.8 | 65.6 | 63.9 | 49.9 | 12.0 |
| 2-chloro-1,1-difluoroethane | 14.7 | 8.8 | 12.5 | 2.4 | 0.1 |
| dimers | 0.36 | 0.14 | 0.22 | 0.01 | 0.00 |
| Sn-derived tar | negligible | negligible | negligible | negligible | negligible |

EXAMPLE 22 AND COMPARATIVE EXAMPLE 5

A 200-ml reactor made of Hastelloy C equipped with a stirrer, a condenser, a thermometer and a pressure gage was used. This reactor was also equipped with a nozzle and valve at the bottom so that the reaction solution obtained at completion of the reaction could be

EXAMPLES 23 TO 26

The procedures of Example 22 were repeated except that the butyl aldehyde was replaced by stannic chloride pentahydrate (Ex. 23), cyclohexyl alcohol (Ex. 24), pyridine (Ex. 25) and triethylamine (Ex. 26). The results are shown in Table 6.

TABLE 6

|  | Ex. 22 | Ex. 23 | Ex. 24 | Ex. 25 | Ex. 26 | Comp. Ex. 5 |
| --- | --- | --- | --- | --- | --- | --- |
| O-containing compound or N-containing compound | butylaldehyde | SnCl$_4$.5H$_2$O | cyclohexyl alcohol | pyridine | triethylamine | none |
| Amount of O- or N-containing compound (mole) | 0.15 | 0.03 | 0.15 | 0.15 | 0.15 | 0 |
| Amount of SnCl$_4$ (mole) | 0.15 | 0.12 | 0.15 | 0.15 | 0.15 | 0.15 |
| HF phase: | lower layer | lower layer | lower layer | lower layer | lower layer | upper layer |
| Cl$^-$ (wt %) | 5.1 | 5.5 | 2.4 | 5.5 | 5.9 | 0.6 |

TABLE 6-continued

|  | Ex. 22 | Ex. 23 | Ex. 24 | Ex. 25 | Ex. 26 | Comp. Ex. 5 |
|---|---|---|---|---|---|---|
| F⁻ (wt %) | 41.7 | 50.5 | 56.7 | 39.2 | 29.5 | 90.6 |
| Sn (wt %) | 24.7 | 35.9 | 27.8 | 26.5 | 20.8 | 1.9 |
| Organic matter (wt %) | ≈0 | ≈0 | ≈0 | ≈0 | ≈0 | ≈0 |
| balance | 28.5 | 8.1 | 13.1 | 28.8 | 43.8 | 6.9 |
| Organic phase: | upper layer | upper layer | upper layer | upper layer | upper layer | lower layer |
| Cl⁻ (wt %) | 1.1 | 2.2 | 0.2 | 0.1 | 0.1 | 6.0 |
| F⁻ (wt %) | 2.1 | 0.8 | 1.3 | 0.4 | 0.3 | 0.4 |
| Sn (wt %) | 2.0 | 2.0 | 0.4 | 0.1 | 0.1 | 5.7 |
| balance (predominantly organic) | 94.8 | 95.0 | 98.1 | 99.4 | 99.5 | 87.9 |
| In organic matter (wt %): |  |  |  |  |  |  |
| 1,1,2-trichloroethane | 78.8 | 61.0 | 91.9 | 76.7 | 86.2 | 34.1 |
| 1,2-dichloro-1-fluoroethane | 20.6 | 37.5 | 4.8 | 22.8 | 13.5 | 60.5 |
| 2-chloro-1,1-difluoroethane | 0.2 | 1.4 | 0.0 | 0.3 | 0.1 | 4.6 |
| dimers | 0.00 | 0.01 | 0.00 | 0.00 | 0.03 | 0.79 |
| Sn-derived tar | negligible | negligible | negligible | negligible | negligible | positive |

EXAMPLE 27

A reactor of the same type as used in Example 11 was charged with 578 g (4.4 moles) of trichloroethylene, 308 g (15.4 moles) of anhydrous hydrogen fluoride, 172 g (0.66 mole) of stannic chloride and 11.9 g (0.66 mole) of water, and reaction was carried out as in Example 11. Two hours later, the reaction was quenched. The reaction solution separated into HF and organic phases, with no detectable tin-derived tar present. The concentrations of Sn in the organic and HF phases were 1.6 wt% and 27.9 wt%, respectively, suggesting that almost all of the Sn present dissolved in the HF phase. The principal reaction products were 1,1,2-trichloro-1-fluoroethane and 1,2-dichloro-1,1-difluoroethane, which were obtained in yields of 33% and 55%, respectively.

EXAMPLE 28

A reactor of the same type as used in Example 1 was charged with 96.9 g (1.0 mole) of trans-1,2-dichloroethylene, 70.0 g (3.5 moles) of anhydrous hydrogen fluoride, 39.1 g (0.15 mole) of stannic chloride and 2.7 g (0.15 mole) of water, and reaction was carried out as in Example 1, except that an oil bath equipped with a thermometer and two 500 W heaters and maintained at 200° C. was used as a heating source in place of the 300 W mantle heater. After completion of the reaction, the reactor was cooled and then the reaction solution was recovered. It had separated into two liquid phases, HF and organic phases. No detectable tin-derived tar was present in the reaction solution, and the concentrations of Sn in the organic phase and HF phase were 0.3 wt% and 33.1 wt%, respectively, suggesting that almost all of the Sn present dissolved in the HF phase. The principal reaction products were 1,2-dichloro-1-fluoroethane and 2-chloro-1,1-difluoroethane, which were obtained in yields of 35% and 6%, respectively. The concentration of dimers in the organic phase was 0.47 wt%.

COMPARATIVE EXAMPLE 6

The procedures of Example 28 were repeated except that no water was added. The reaction solution obtained at completion of the reaction was rich in higher boiling substances, oligomers, black precipitates and tin-derived tar and did not separate into two liquid phases. This solution was poured into water to cause separation into aqueous and organic phases. The organic phase contained 38.4 wt% of 1,2-dichloro-1-fluoroethane, 19.2 wt% of 2-chloro-1,1-difluoroethane and 31.8 wt% of dimers. Apparently, the concentration of dimers was markedly higher than that in Example 28.

EXAMPLE 29

A reactor of the same type as used in Example 28 was charged with 96.9 g (1.0 mole) of vinylidene chloride, 50.0 g (2.5 moles) of anhydrous hydrogen fluoride, 39.1 g (0.15 mole) of stannic chloride and 2.7 g (0.15 mole) of water, and reaction was performed for 1 hour as in Example 28, except that the reaction pressure rose to 34 kg/cm²G since at no stage of the reaction was the by-product hydrogen chloride withdrawn from the reactor.

After completion of the reaction, the reactor was cooled and the reaction solution was recovered. Since the pressure in the reactor was higher than one atmosphere, the valve was opened to trap gaseous products. No detectable tin-derived tar was present in the reaction solution. The principal reaction products were 1,1-dichloro-1-fluoroethane and 1-chloro-1,1-difluoroethane, which was obtained in yields of 29% and 34%, respectively.

EXAMPLE 30

A reactor of the same type as used in Example 22 was charged with 78.2 g (0.30 mole) of stannic chloride, 5.4 g (0.30 mole) of water and 80.0 g (4.0 moles) of anhydrous hydrogen fluoride, and reaction was performed as in Example 22. Two hours after the start of the reaction, the heater was turned off and the reaction solution was recovered. It had a homogeneous phase with Sn having dissolved completely to give a concentration of 31.1 wt%. Although no hydrocarbon halide was supplied, Sn converted to a new form.

Half of the reaction solution was charged into the reactor which was subsequently fed with 133 g (1.0 mole) of 1,1,2-trichloroethane. Reaction was carried out as in Example 22. The reaction solution separated into HF and organic phases, with Sn being present in the HF and organic phases in concentrations of 36.3 wt% and 1.6 wt%, respectively. Neither phase contained a detectable amount of tin-derived tar. The conversion of 1,1,2-trichloroethane was 51% and the yields of 1,2-dichloro-1-1-fluoroethane and 2-chloro-1,1-difluoroethane were 48% and 2%, respectively. No dimer was detected in the organic phase.

EXAMPLE 31

A 10-ml reactor made of Hastelloy C was charged with 2.7 g (0.02 mole) of 1,1,2-trichloroethane, 0.80 g (0.04 mole) of anhydrous hydrogen fluoride, 0.54 g (0.003 mole) of tetramethyl tin and 0.054 g (0.003 mole) of water. The hermetically sealed reactor was immersed in an oil bath preheated at 100° C. The temperature of the oil bath was slowly raised to 160° C. in about 1 hour, and maintained at that temperature in the subsequent stage of reaction. Three hours after the immersion in the oil bath, the reactor was recovered and cooled. The reaction solution was then poured into water to cause separation into aqueous and organic phases. The organic phase consisted of 90.5 wt% of 1,1,2-trichloroethane, 9.4 wt% of 1,2-dichloro-1-fluoroethane and 0.1 wt% of 2-chloro-1,1-difluoroethane.

EXAMPLE 32

Stannic chloride was added to 1,1,2-trichloroethane to give a molar ratio of 0.15/1 (stannic chloride/1,1,2-trichloroethane). To the resulting mixture, sec-butyl alcohol was added in an amount equimolar to that of stannic chloride. Two separate streams of this mixture and anhydrous hydrogen fluoride were fed continuously into a reactor of the same type as used in Example 11, except that it was equipped with a level gage, at flow rates of 667 g/hr and 300 g/hr, respectively. The voltage supplied to the mantle heater was held at a constant value of 70 volts so as to heat the reactor. The reaction pressure was maintained at a constant level of 10 kg/cm$^2$G and the by-product hydrogen chloride was continuously withdrawn after condensing the anhydrous hydrogen fluoride entrained in the condenser. The temperature of the reaction solution was held at temperatures between 98° C. and 102° C. throughout the reaction. The reaction solution was continuously withdrawn from the reactor through the bottom nozzle. The withdrawn reaction solution was transferred to a receptacle, whereupon it separated into HF and organic phases, with no detectable tin-derived tar present. Under these conditions, the reaction was performed in a continuous manner for 11 hours. The recovered HF phase contained 19.8 wt% of Sn while the Sn concentration in the organic phase was 2.6 wt%, suggesting that the greater part of the Sn present dissolved in the HF phase. The concentrations of 1,2-dichloro-1-fluoroethane and 2-chloro-1,1-difluoroethane in the organic phase was 25.6 wt% and 0.8 wt%, respectively. The remainder was substantially composed of the starting material (1,1,2-trichloroethane) and no dimer was detectable at all.

COMPARATIVE EXAMPLE 7

The procedures of Example 32 were repeated except that no sec-butyl alcohol was added. When six hours passed after commencing the continuous reaction, the temperature in the reactor increased sharply and no further performance of the reaction was possible. After cooling, the reactor was opened and a tar-like substance was found in the reactor. This substance was analyzed to be Sn-derived tar containing 28.7 wt% of Sn, 0.5 wt% of Cl$^-$, 8.8 wt% of F$^-$ and 54.2 wt% of an organic matter. This tar also contained as much as 1.1 wt% of a black precipitate that was not dissolve in either water or acetone.

The reaction solution leaving the reactor separated into the HF phase, the organic phase and a tar-like substance. The HF phase contained only 0.8 wt% of Sn whereas the organic phase and the tar-like substance contained 6.7 wt% and 24.2 wt%, respectively, of Sn. The tar-like substance was also tin-derived tar. The organic phase contained 35.1 wt% of 1,2-dichloro-1-fluoroethane and 2.3 wt% of 2-chloro-1,1-difluoroethane. The concentration of dimers in the organic phase was 0.7 wt% which was significantly higher than the value found in Example 32.

EXAMPLE 33

Figure 5:
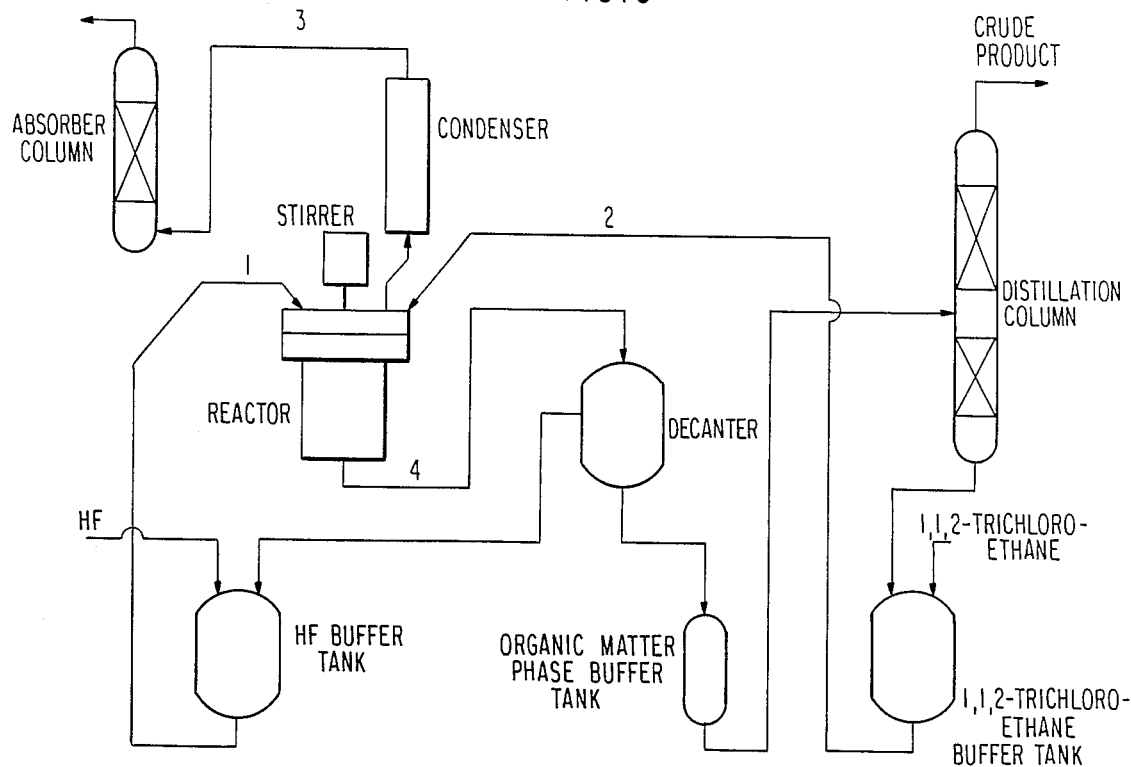
FIG. 5 shows a flowsheet of the process employed in Example 33.

Continuous reaction was performed by a process the flowsheet of which is depicted in FIG. 5. The reactor was a 1000-ml reactor made of Hastelloy C of the same type as used in Example 32 and was equipped with a pressure gage, a thermometer, a level gage and a stirrer. This reactor was so designed that anhydrous hydrogen fluoride containing the novel tin catalyst could be continuously fed through line 1 while an organic matter that was predominantly composed of 1,1,2-trichloroethane could be continuously supplied through line 2. The by-product hydrogen chloride would come into an absorption column through line 3 after removing the entrapped anhydrous hydrogen fluoride by condensation in a condenser through which a coolant (about −10° C.) was circulated. The reaction solution would be continuously withdrawn through the reactor through line 4 and separated into HF and organic phases in a decanter. The separated HF phase would enter an HF buffer tank, combine with makeup anhydrous hydrogen fluoride and would be recycled to the reactor. The organic phase separated from the HF phase in the decanter would come into a distillation column where it would be separated into the crude product and the starting material (1,1,2-trichloroethane), which would then enter a 1,1,2-trichloroethane buffer tank, combine with makeup 1,1,2-trichloroethane and would be recycled to the reactor.

The HF phase that was prepared in Example 32 and which contained the novel tin catalyst was charged into both the reactor and the HF buffer tank. After charging 1,1,2-trichloroethane into both the reactor and the 1,1,2-trichloroethane buffer tank, continuous reaction was commenced. The voltage supplied to the mantle heater was held at 70 volts and the reaction pressure was maintained at 10 kg/cm$^2$G. The reaction temperature was between 98° C. and 102° C. The rates of supply of 1,1,2-tichloroethane and anhydrous hydrogen fluoride were about 480 g/hr and 290 g/hr, respectively.

Continuous reaction was sustained under the aforementioned conditions for 62 hours. The novel tin catalyst dissolved in the HF phase and could be recycled through the loop of the reactor—decanter—HF buffer tank without experiencing any drop in the catalytic activity. After turning off the equipment, the reactor, decanter and the HF buffer tank were opened, and no detectable tin-derived tar or black precipitate was present. In the reaction, 6,780 g of 1,1,2-trichloroethane was consumed, and the amounts of 1,2-dichloro-1-fluoroethane and 2-chloro-1,1-difluoroethane produced were 5,040 g (yield: 85%) and 88 g (yield: 2%), respectively. No dimer was detected in any of the organic phases present in the reactor and 1,1,2-trichloroethane buffer tank.

EXAMPLE 34

Figure 6:
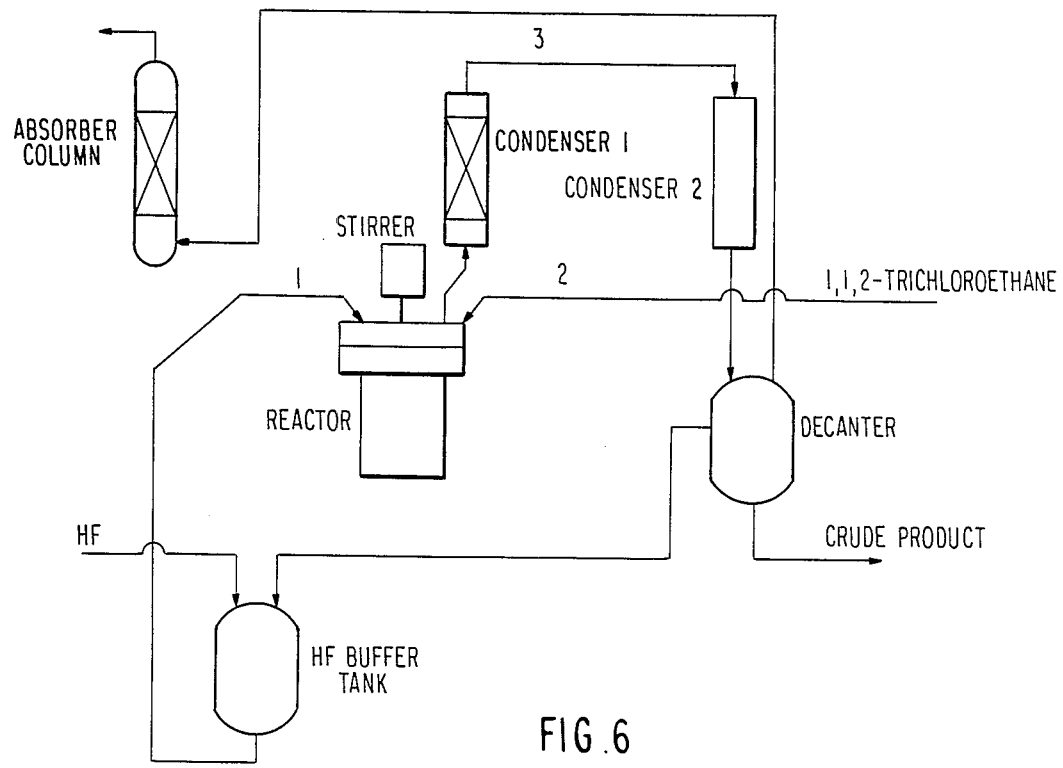
FIG. 6 shows a flowsheet of the process employed in Example 34.

A reactor of the same type as used in Example 33 was employed in performing continuous reaction by a process the flowsheet of which is depicted in FIG. 6. The reactor was so designed that anhydrous hydrogen fluoride and 1,1,2-trichloroethane could be continuously supplied through lines 1 and 2, respectively. A condenser 1 positioned above the reactor 1 was packed with HELI PACK No. 2 (produced by Tokyo Special Wire Netting Co., Ltd.) and warm water instead of coolant (about −10° C.), was circulated through this condenser to provide for temperature control. The resulting gaseous 1,2-dichloro-1-fluoroethane and 2-chloro-1,1-difluoroethane would be withdrawn from the top of the condenser 1 through line 3 together with hydrogen chloride and anhydrous hydrogen fluoride, and would be condensed in a condenser 2 through which a coolant (about −10° C.) was circulating. The condensed crude product and anhydrous hydrogen fluoride would be separated into two liquid HF and organic phases in a decanter, and the anhydrous hydrogen fluoride would combine with makeup anhydrous hydrogen fluoride in an HF buffer tank and be recycled to the reactor. The hydrogen chloride not already condensed in the condenser 2 would be absorbed in an absorber column.

The HF phase that was prepared in Example 32 and which contained the novel tin catalyst was charged into the reactor, and after supplying anhydrous hydrogen fluoride into the HF buffer tank, continuous reaction was commenced. The voltage supplied to the mantle heater was held at 40-60 volts and the reaction pressure was maintained at 5-10 kg/cm²G. Into the reactor, 1,1,2-trichloroethane and anhydrous hydrogen fluoride were supplied at such flow rates that the level in the reactor and the temperature of the reaction solution were at substantially constant levels. The reaction temperature depended on the reaction pressure and was at 75°-80° C. for 5 kg/cm²G, and at 98°-103° C. for 10 kg/cm²G. The condenser 1 was held at 60°-90° C. and hydrogen fluoride and an organic matter were distilled together with the by-product hydrogen chloride. The rate of distillation of the organic matter was 20-70 g/hr and that of hydrogen fluoride was 1.4-2.7 times (by weight) the value for the organic matter distillate.

HELI PACK No. 2 in the condenser 1 was responsible for a certain degree of separation between the starting 1,1,2-trichloroethane and each of the products 1,2-dichloro-1-fluoroethane and 2-chloro-1,1-difluoroethane, and the organic distillate contained 60-90 wt% of 1,2-dichloro-1-fluoroethane and 1-8 wt% of 2-chloro-1,1-difluoroethane. The reaction solution contained 13-24 wt% of Sn but the hydrogen fluoride distillate contained only 0.0-0.6 wt% of Sn, suggesting the substantial absence of distillation of the novel tin compound.

After performing continuous reaction for 36 hours, the reactor was opened and it was found that no detectable tin-derived tar or black precipitate was present. No dimer was detected in the organic matter in the reactor.

In the reaction, 2,290 g of 1,1,2-trichloroethane was consumed and the amounts of 1,2-dichloro-1-fluoroethane and 2-chloro-1,1-difluoroethane produced were 1,440 g (yield: 72%) and 92 g (yield: 5%), respectively.

While the invention has been described in detail and with reference to specific embodiments thereof, it will be apparent to one skilled in the art that various changes and modifications can be made therein without departing from the spirit and scope thereof.

What is claimed is:

1. A process for producing a hydrocarbon fluoride which comprises reacting a hydrogen-containing hydrocarbon halide with anhydrous hydrogen fluoride in a liquid phase in the presence of reaction product of (i) at least one of (a) an oxygen-containing compound selected from the group consisting of H₂O, H₂O₂ and an oxygen-containing organic compound selected from the group consisting of alcohols, ketones, carboxylic acids, aldehydes, ethers, esters and epoxy compounds, and (b) a nitrogen-containing compound selected from the group consisting of HN₃ and a nitrogen-containing organic compound, (ii) a tin compound selected from the group consisting of a stannic halide, a stannic oxyhalide and an organotin compound, and (iii) anhydrous hydrogen fluoride, said reaction product being soluble in anhydrous hydrogen fluoride.

2. A process according to claim 1, wherein the tin compound is a stannic halide.

3. A process according to claim 1, wherein the tin compound is stannic chloride.

4. A process according to claim 1, wherein the oxygen-containing compound is H₂O.

5. A process according to claim 1, wherein the oxygen-containing organic compound is an alcohol.

6. A process according to claim 5, wherein the alcohol is a monohydric alcohol.

7. A process according to claim 1, wherein the nitrogen-containing organic compound is pyridine or triethylamine.

8. A process according to claim 1, wherein the hydrogen-containing hydrocarbon halide is represented by formula (I)

wherein X represents a halogen atom other than F; R¹ represents a hydrogen atom, a halogen atom, a hydrocarbon group, or a hydrocarbon halide group; and R² and R³ each represents a halogen atom, a hydrocarbon group, or a hydrocarbon halide group.

9. A process according to claim 8, wherein the hydrogen-containing hydrocarbon halide is 1,1,1-trichloroethane.

10. A process according to claim 8, wherein the hydrogen-containing hydrocarbon halide is 1,1,1,2-tetrachloroethane.

11. A process according to claim 1, wherein the hydrogen-containing hydrocarbon halide is represented by formula (II)

wherein X represents a halogen atom other than F; and R⁴ and R⁵ each represents a hydrogen atom, a halogen atom, a hydrocarbon group, or a hydrocarbon halide group.

12. A process according to claim 11, wherein the hydrogen-containing hydrocarbon halide is 1,1,2-trichloroethane.

13. A process according to claim 11, wherein the hydrogen-containing hydrocarbon halide is 1,2-dichloro-1-fluoroethane.

14. A process according to claim 1, wherein the hydrogen-containing hydrocarbon halide is represented by formula (III)

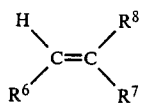 (III)

wherein $R^6$ represents a hydrogen atom, a halogen atom, a hydrocarbon group, or a hydrocarbon halide group; and $R^7$ and $R^8$ each represents a halogen atom, a hydrocarbon group, or a hydrocarbon halide group, provided that $R^7$ and $R^8$ are not a hydrocarbon groups at the same time when $R^6$ is a hydrogen atom or a hydrocarbon group.

15. A process according to claim 14, wherein the hydrogen-containing hydrocarbon halide is 1,1-dichloroethylene.

16. A process according to claim 14, wherein the hydrogen-containing hydrocarbon halide is trichloroethylene.

17. A process according to claim 1, wherein the hydrogen-containing hydrocarbon halide is represented by formula (IV-1) or (IV-2):

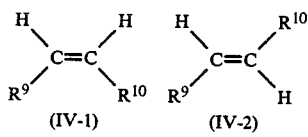

wherein $R^9$ and $R^{10}$ each represents a hydrogen atom, a halogen atom, a hydrocarbon group, or a hydrocarbon halide group, provided that $R^9$ and $R^{10}$ are not a hydrogen atom and/or a hydrocarbon group at the same time.

18. A process according to claim 17, wherein the hydrogen-containing hydrocarbon halide is 1,2-dichloroethylene.

19. A process according to claim 1, wherein the reaction pressure ranges from 3 to 30 kg/cm²G.

20. A process according to claim 1, wherein the reaction temperature ranges from 50° to 200° C.

21. A process according to claim 1, wherein the molar ratio of F to Sn in the reaction liquid ranges from 6/1 to 100/1.

22. A process according to claim 1, wherein the molar ratio of O to Sn in said reaction product ranges from 0.2/1 to 2/1.

23. A process according to claim 1, wherein the oxygen-containing compound is H₂O or an alcohol, the tin compound is a stannic halide, the hydrogen-containing hydrocarbon halide is 1,1,2-trichloroethane, and the molar ratio of O to Sn in said reaction product is in the range of from 0.2/1 to 2/1.

24. A process according to claim 1, wherein the oxygen-containing compound is H₂O or an alcohol, the tin compound is a stannic halide, the hydrogen-containing hydrocarbon halide is 1,1-dichloroethylene or 1,1,1-trichloroethane, and the molar ratio of O to Sn in said reaction product is in the range of from 0.2/1 to 2/1.

25. A process according to claim 1, wherein the hydrogen-containing hydrocarbon halide is a hydrogen-containing hydrocarbon chloride and by-produced hydrogen chloride is continuously withdrawn from the reaction system.

26. A process according to claim 1, wherein the hydrocarbon fluoride produced is withdrawn from the reaction system in the form of vapor.

27. A process according to claim 1, wherein the reaction solution obtained by reacting the hydrogen-containing hydrocarbon halide with anhydrous hydrogen fluoride in a liquid phase in the presence of said reaction product is separated into an organic phase predominantly composed of a hydrocarbon halide and a hydrogen fluoride phase predominantly composed of said reaction product and anhydrous hydrogen fluoride, and the hydrocarbon fluoride is obtained from the organic phase.

28. A process according to claim 27, wherein the hydrogen fluoride phase is recycled to the reaction system.

29. A process according to claim 1, wherein the hydrogen-containing hydrocarbon halide is continuously reacted with anhydrous hydrogen fluoride.

30. A process according to claim 1, wherein the oxygen-containing organic compound is selected from the group consisting of methyl alcohol, ethyl alcohol, propyl alcohol, butyl alcohol, ethylene glycol, acetone, methyl ethyl ketone, formic acid, acetic acid, propionic acid, formaldehyde, butyaldehyde, methyl ether, ethyl ether, tetrahydrofuran, 1,4-dioxane and ethylene glycol monoethyl ether.

31. A process according to claim 1, wherein the nitrogen-containing compound is selected from the group consisting of pyridine, triethylamine, sec-butylamine, hexamethylenediamine, aniline, toluidine and triethanolamine.

32. A process according to claim 1, wherein the hydrogen-containing hydrocarbon halide is represented by formula (I)

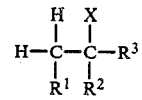 (I)

wherein X represents a halogen atom other than F; $R^1$ represents a hydrogen atom, a halogen atom, a hydrocarbon group, or a hydrocarbon halide group; and $R^2$ and $R^3$ each represents a halogen atom, a hydrocarbon group, or a hydrocarbon halide group; or formula (II)

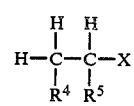 (II)

wherein X represents a halogen atom other than F; and $R^4$ and $R^5$ each represents a hydrogen atom, a halogen atom, a hydrocarbon group, or a hydrocarbon halide group.

33. A process according to claim 1, wherein the tin compound is a stannic halide or an organotin compound.

34. A process according to claim 12, wherein the hydrocarbon fluorides produced by said process are 1,2-dichloro-1-fluoroethane and 2-chloro-1,1-difluoroethane.

* * * * *